United States Patent [19]
Li et al.

[11] Patent Number: 5,830,177
[45] Date of Patent: Nov. 3, 1998

[54] SKIN VIBRATION METHOD FOR TOPICAL TARGETED DELIVERY OF BENEFICIAL AGENTS INTO HAIR FOLLICLES

[75] Inventors: Lingna Li; Eugene Baranov, both of San Diego, Calif.

[73] Assignee: AntiCancer, Inc., San Diego, Calif.

[21] Appl. No.: 755,139

[22] Filed: Nov. 22, 1996

[51] Int. Cl.$^6$ ................................................. A61B 17/20
[52] U.S. Cl. ............................ 604/22; 601/17; 604/49
[58] Field of Search ...................... 604/20–22; 606/33; 607/3, 97–100, 108–110; 601/1–2, 17, 46

[56] References Cited

U.S. PATENT DOCUMENTS

| | | | |
|---|---|---|---|
| 3,727,607 | 4/1973 | Dill | 601/57 |
| 4,186,733 | 2/1980 | Mogaki | 601/46 |
| 5,076,305 | 12/1991 | Williams . | |
| 5,165,131 | 11/1992 | Staar . | |
| 5,311,632 | 5/1994 | Center . | |
| 5,400,466 | 3/1995 | Alderman et al. . | |
| 5,421,726 | 6/1995 | Okada . | |
| 5,538,503 | 7/1996 | Henley | 604/20 |

FOREIGN PATENT DOCUMENTS

| | | | |
|---|---|---|---|
| 1144708 | 3/1985 | U.S.S.R. | 601/46 |
| 1602522 | 10/1990 | U.S.S.R. | 601/46 |
| 1444985 | 8/1976 | United Kingdom | 601/78 |

OTHER PUBLICATIONS

Mann et al., *Cell*, 73:249–261 (1993).

*Primary Examiner*—Mark Bockelman
*Attorney, Agent, or Firm*—Morrison & Foerster

[57] ABSTRACT

The present invention provides a methods and apparatuses for use in providing rapid, selective and effective targeted delivery of beneficial substances into hair follicles. The invention relies on the use of vibrational method of delivery of substances of different size from small molecules up to particles compatible with the diameter of hair strand into the hair bulb. The skin is subjected to the vibration of about 1 Hz to about 100 Hz frequency and 0.1 mm to about 10 mm amplitude, an amount which is sufficient to cause mechanical shifts in different directions of skin structure without damage. This results in follicle effective uptake of the tested substances such as carbon particles of different size as well as melanin. The methods and apparatuses of the present invention are particularly useful in conjunction with photosensitive agents and electromagnetic irradiation. Such a combination is used to target the delivery of the agent to within hair follicles and then subsequently activate the agent.

14 Claims, 11 Drawing Sheets

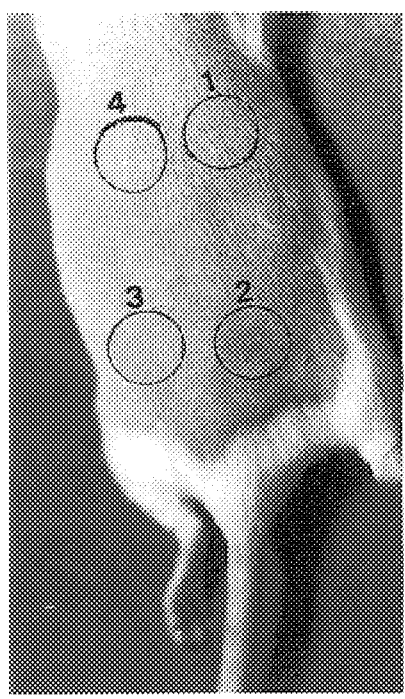
FIG. 6A
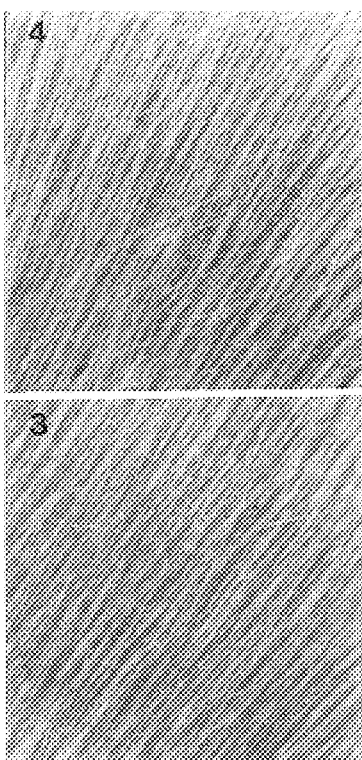
FIG. 6B
FIG. 6C
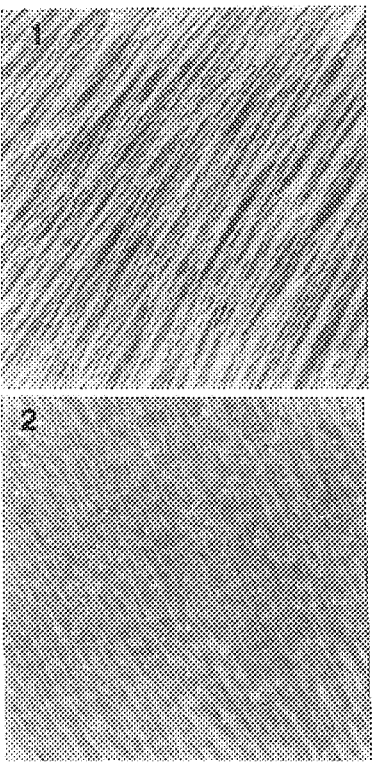
FIG. 6D
FIG. 6E

SKIN VIBRATION METHOD FOR TOPICAL TARGETED DELIVERY OF BENEFICIAL AGENTS INTO HAIR FOLLICLES

TECHNICAL FIELD

The present invention relates to field of delivering compositions selectively to hair follicles. The present invention specifically provides methods and apparatuses for use in the delivery of beneficial agents to hair follicles.

BACKGROUND ART

Treatment of the hair and skin with various creams or lotions with biologically active ingredients to improve hair growth and other conditions have generally low efficiency. A wide variety of externally applied agents are available for application to the hair to improve body, flexibility, curl, etc. These have limited and only short-term usefulness. Coloring hair with various dyes, that may be carcinogenic, requires frequent repetitions and is not always natural in appearance.

The use of biologically active compounds that are hair growth stimulators or that change other hair characteristics, such as color, would seem to be a more natural and attractive approach, especially at the stage where hair-follicle cells still exist but hair growth, for unknown reasons, is adversely affected. Attempts to follow this approach have been ineffective, possibly because of the inability of stimulators to penetrate the cellular membrane of hair follicle cells and to enter into the cells where their action is needed.

There is a need for improved methods of delivering compositions to hair follicles as a means of administering agents that affect hair growth, color and appearance. In general, the methods currently used for the topical delivery of biologically active substances to hair follicles are mainly based on diffusion of substances or their complexes with lipids. However diffusion of particles over large distances even for small particles is a very slow process. For example, the root mean square distance covered by particles such as small molecules with a typical diffusion coefficient $5\ 10^{-6}$ $cm^2 s^{-1}$ for 1 day is only 1 cm. Accordingly, passive diffusion is not efficient for delivering particles of sizes 0.5 um and larger to hair follicles.

Other methods that have been proposed for delivering agents to hair follicles, such as electroporation and the use of high pressure, results in the transdermal delivery of the substance to the systemic circulation are not specific for selective targeting of hair follicles. Accordingly, there is a present need for methods and apparatuses that selectively administer agents to hair follicles.

DISCLOSURE OF THE INVENTION

The present invention provides improved methods and apparatuses for selectively delivering agents, such as, therapeutic, cosmetic or other beneficial compounds, to hair follicles. The present invention is based on the observation that vibration applied to the surface of skin containing hair follicles greatly increases the rate, selectivity and efficiency of delivering agents to hair follicles. Based on this observation, the present invention provides improved methods for delivering agents to hair follicles comprising the step of providing vibration to the skin containing the hair follicle using vibration means in combination with the agent.

The present invention further provides apparatuses for use in selectively delivering agents to hair follicles. The apparatuses of the present invention comprise a vibration means for applying vibration to the skin and application means for applying the agent to the skin.

BRIEF DESCRIPTION OF THE DRAWINGS

FIG. 6 shows the effect of laser radiation to prevent hair growth.

BEST MODE FOR CARRYING OUT THE INVENTION

Figure 1:
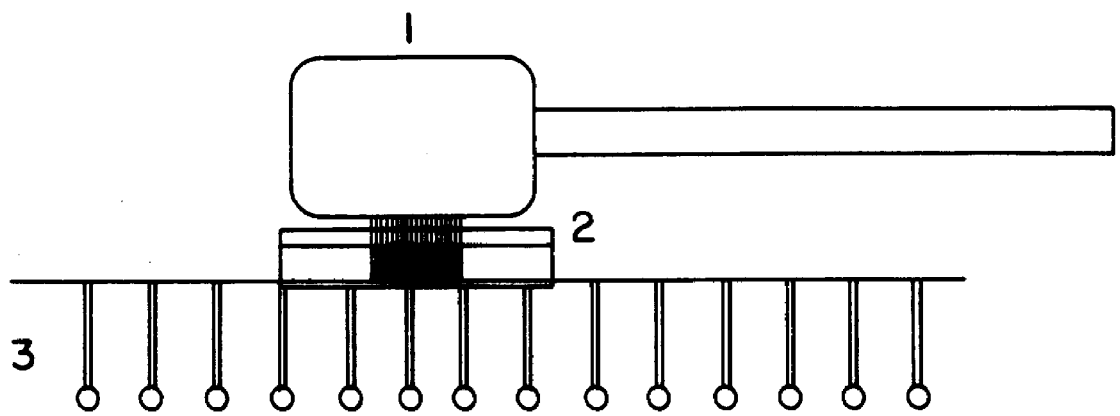
FIG. 1 illustrates the experimental conditions on mice skin: 1—vibrator with the bristles; 2—chamber with substance; 3—mouse skin, with hair strands removed

The present invention is based on the observation that the selective administration of an agent into hair follicles can be greatly increased by applying vibration to the skin surface containing the hair follicles at the time or shortly after the agent is applied to the skin surface. Based on this observation, the present invention provides improved methods and apparatuses for selectively delivering agents to hair follicles.

In detail, in one embodiment, the present invention provides improved methods for delivering an agent to hair follicles wherein the improvement comprises the step of applying vibration from about 1 Hz to about 100 Hz with an amplitude of about 0.1 mm to about 10 mm in combination with said agent. The vibration applied is sufficient to cause mechanical shifts in different directions of skin structure without damage to the hair follicle.

As used herein, hair follicles are defined as structures in dermal tissues from which hair grows. The methods and apparatuses of the present invention can be used with hair follicles regardless of the location of the skin containing the hair follicle. For example, the methods and apparatuses can be used to deliver agents to hair follicles located on the scalp, pubic areas, legs, face and back, as well as on other parts of the body.

The present invention can be used to deliver agents to hair follicles regardless of whether there is presently hair growth from the follicle. In many uses of the methods and apparatuses of the present invention, an agent will be delivered to a hair follicle that does not have hair growth. In other uses, an agent will be delivered to a hair follicle that has hair growth. In the Examples, effective delivery to hairless hair follicles (waxed mouse) and hair containing hair follicles (cut hair mouse) was demonstrated.

The present invention relies on applying vibration from about 1 Hz to about 100 Hz to the surface of the skin while the agent is being administered, or shortly after the agent is administered. Any device means known in the art for applying vibration to a surface can be adapted and used in the present invention. In the examples that follow, a Body- Mate™ Power messager, model PM-606 vibration brush (HomeMedics Inc., 2240 Greer Blvd. Keego Harbor, Mich. 48320) was used.

Devices means known in the art for applying vibration to a surface produce vibration through any of a variety of methods. Such methods include, but are not limited to, vibrations produced from a spinning acentric weight, vibration produced by applying electrical energy to a piezoelectric crystal, and vibration produced through use of acoustic waves such as a speaker, for example see U.S. Pat. Nos. 5,165,131, 5,076,305, 5,421,726, 5,400,466 and 5,311,632, all of which are incorporated by referenced. Each of the device means can be adapted for use in the present invention.

The vibration applied to the skin surface will preferably have a vibration frequency from about 1 Hz to about 100 Hz. The most preferred vibration frequency is about 10 Hz. A skilled artisan can readily use frequency modulator means known in the art to tune the vibration frequency of the apparatus to be within the appropriate range. The optimization of the vibration frequency used is a matter of routine practice and can be readily determined using any particular agent or composition.

The amplitude of the applied vibration is preferably from about 0.1 mm to about 10 mm. The most preferred amplitude of vibration is about 1 mm. A skilled artisan can readily employ amplitude modulator means known in the art in order to vary the amplitude of the vibration applied. The optimization of the amplitude of the vibration used is a matter of routine practice and can be readily determined using any particular agent or composition.

In the present method, vibration is applied to the surface of the skin in combination with the agent or shortly after the agent is applied to the skin. Vibration can be applied in either a circular motion, in a static position, or in a back-and-forth motion. A skilled artisan can readily use any of a variety of methods for applying vibration to a target area of the skin or to the entire surface of the skin that is treated.

Vibration is applied to skin for a sufficient time to cause mechanical shifts in different directions of skin structure without damage to the hair follicle. The length of time required will vary based on the nature of the agent and its formulation, particularly size of the agent, and the amplitude and frequency of vibration used. In general, vibration will be applied from about 1 minute to about 10 minutes, although shorter or longer time can be used or may be necessary. A skilled artisan can readily determine the optimum time needed fro the effective/selective administration of the agent to hair follicles.

The vibration is applied at the same time as the agent or shortly after the agent is administered to the skin. The timing of the application of vibration will be determined primarily by the nature of the agent/composition and the location of the treated skin.

The methods and apparatuses of the present invention are used to selectively administer an agent to a hair follicle. As used herein, an agent is said to be selectively administered to a hair follicle when the agent is delivered to a hair follicle at a rate that is preferably 10 times greater than to areas other than the hair follicle. Preferably, the agent will be administered at a rate 100 times greater than to non-hair follicle. Most preferably, the administered agent will only be found in hair follicles following application of the vibration and removal of excess agent.

The present method can be used with any of a variety of agents that are intended to be selectively delivered to hair follicles. Such agents generally fall within the categories of hair growth stimulators, hair growth inhibitors, genes for regulating hair growth, antialopecia agents, agents to restore natural hair pigment, agents to modify the color of hair and agents to remove unwanted hair.

It is contemplated that the methods and apparatuses of the present invention can be used to deliver of a wide variety of beneficial or otherwise therapeutic compounds to the hair follicle, with the selectivity of delivery to the hair follicle over adjacent skin tissue cells being of particular importance. Thus, the therapeutic compounds can be nucleic acids, hormones, proteins, enzymes, vitamins and other biochemical co-factors deemed to provide a therapeutic effect upon the hair follicle cell's growth, condition, color and the like. A summary of such agents is provided in issued U.S. Pat. No. 5,641,508 (U.S. Ser. No. 08/181,471, herein incorporated by reference).

Particularly preferred are agents that improve the growth of the hair shaft, agents that stimulate the production of hair coloring pigments in the hair follicle, agents that replace pigment in the follicle cell or hair shaft (i.e., restore hair color), agents that stimulate hair growth, and agents that prevent or enhance hair loss.

Agents useful for pigmenting hair color include, but are not limited to, the protein melanin, which directly colors hair as a pigment, and the protein tyrosinase, which is an enzyme which catalyzes the production of melanin pigment precursors and thereby increases pigment production in hair follicle cells, inhibitors of melanogenesis and nucleic acids which encode and express tyrosinase and other proteins that stimulate or inhibit hair growth or prevent hair loss.

Agents useful in conditions of hair loss (alopecia) are those which stimulate hair growth, or those which inhibit the hair loss. Hair growth stimulators are generally well known, and include, but are not limited to, minoxidil, substance-P, fenesteride, cyclosporin, p21 protein, cell cycle inhibitors, cell proliferation inhibitors, anti-androgen agents, inhibitors of 5-α reductase and the like known hair growth stimulators.

A preferred embodiment involves the prevention of hair loss (alopecia) during chemotherapy where a patient experiences chemotherapy-induced hair loss due to the effect of the chemotherapeutic agent on the hair follicle and surrounding tissue. Thus the invention contemplates the use of inhibitors of the deleterious effects of a chemotherapeutic agent. By virtue of the selective application of the inhibitor to the hair follicle by the methods and apparatuses of the present invention, inhibition of a chemotherapeutic agent is localized to the hair follicle and therefore does not interfere with the intended systemic activity of the administered chemotherapeutic agent. In this embodiment, preferred inhibitors of chemotherapy-induced alopecia are the p21 protein, cell cycle inhibitors, cell proliferation inhibitors, anti-androgen agents, inhibitors of 5-α reductase and a gene product of the multiple drug resistance (MDR) gene, preferably the p-glycoprotein expressed by the human MDR-1 gene. Administration of a nucleic acid comprising an expression vector capable of expressing human p-glycoprotein via the methods and apparatuses of the present invention to the hair follicle provides intracellular human p-glycoprotein, and reduces the toxic effects of the chemotherapy upon the hair follicle, thereby reducing alopecia induced by the chemotherapy.

Another embodiment contemplates the use of the human transformation growth factor-alpha (TGF-α) gene to reverse the "wavy" hair phenotype or the use of other similar growth factors. See for example, Mann et al., *Cell*, 73:249–261 (1993).

The invention additionally contemplates the administration of any gene beneficial to hair follicles. A gene is beneficial to hair follicles where it confers, upon selective delivery to the hair follicles by the present methods, a beneficial effect upon the hair follicle. Exemplary beneficial genes include genes normally and preferentially expressed in hair follicle, and therefore important for normal gene function. Beneficial genes can be identified by any of a variety of molecular biological methods. For example, a cDNA library of expressed genes can be prepared from hair follicle tissue supporting healthy hair, and can be enriched by subtractive hybridization against a cDNA library derived from a non-hair-producing or vellus-hair-producing follicle tissue, thereby producing a library of cDNA molecules whose expression is specific to hair follicles.

The agents that are administered using the methods and apparatuses of the present invention can be formulated using any art known method. Such methods include, but are not limited to, compounding with hydophobic carriers, compounding with aqueous carries and incorporation into liposomes. A skilled artisan can readily use art known formulation methods to obtain an agent for use in the present methods and apparatuses.

The methods and apparatuses of the present invention can be used on any mammal in which delivery of an agent to a hair follicle is needed. Suitable mammals include, but are not limited to, agricultural stock, such as cow, sheep, horse, goat, pig, and the like; pets, such as cats, dogs; other domesticated mammals; and humans. The preferred mammal that is to be treated using the methods and apparatuses of the present invention are human. Typically, the hair follicle is present in the skin of a mammal, and the method is practiced in vivo on a living mammal for the purpose of altering the condition of the hair follicle or hair shaft of the mammal.

The methods and apparatuses of the present invention are particularly useful in delivering photosensitizing, photoreactive and photoactivated agents into hair follicles and the subsequent use of electromagnetic irradiation to activate the compound (hereinafter all such photo-enhanced agents will be referred to as photosensitizing agents). Specifically, following or during administration of such an agent and vibration, irradiation is applied to the treated surface.

As used herein, a photosensitizing agent is defined as an agent that is either inactive and becomes activated upon irradiation with an appropriate wavelength of electromagnetic irradiation, which provides an effect only in the presence of or after electromagnetic irradiation, or which stimulate the absorption of irradiation by surrounding tissues. For example, some agents or cleaved to generate an active form by irradiation whereas others absorb irradiation and release the energy in the surrounding areas. By selectively and efficiently delivering agents into hair follicles, the present methods and apparatuses can be used in combination with irradiation means for selectively delivering and activating an agent in a hair follicle.

As used herein, electromagnetic irradiation, or irradiation, refers to the entire electromagnetic spectrum, regardless of whether it is coherent or incoherent irradiation. The choice of the irradiation wavelength will be based primarily on the photosensitizing agent employed. The preferred irradiation wavelengths include, but are not limited to, the infrared, visible and ultraviolet spectrums. A skilled artisan can readily match an irradiation wavelength with a photosensitizing agent for use in the present methods and apparatuses. In the examples, a continuous pulsing laser, model LT 100-A (LORAD, Danbury, Conn.) Power 2.7 J/cm$^2$, wavelength of 1060 nm, was used to deliver irradiation in pulsed doses to the treatment area.

The choice of the photosensitizing agent will be based on the desired effect. In general, the methods will be used to ablate hair follicles for the subsequent repression of unwanted hair growth. Accordingly, photosensitizing agents that kill surrounding cells are preferred.

The irradiation will be provided to the treated surface concurrently or shortly following the application of the agent and vibration. In general, it is preferable to remove excess agent from the skin prior to the administration of the irradiation.

The irradiation will be provided to the skin for the length of time necessary to activate the photosensitizing agent. A skilled artisan can readily determine the optimum length of irradiation that is needed.

The present invention further provides apparatuses for use in the methods of the present invention. Specifically, the present invention provides apparatuses that contains vibration means for applying vibration to a skin surface and application means for applying an agent to the skin surface.

As used herein, vibration means is defined as any means that can be used to apply vibration to the skin surface. As discussed above, such means include, but are not limited to, vibration produced by an acentric spinning weight, acoustic waves, and piezoelectric crystal (for example see U.S. Pat. Nos. 5,165,131, 5,076,305, 5,421,726, 5,400,466 and 5,311,632, all of which are incorporated by referenced). A skilled artisan can readily adapt any vibration means for use in the present apparatuses.

The apparatuses of the present invention will preferably have amplitude control means and frequency control means. Amplitude control means allows one to fine-tune the amplitude of the vibration produced by the apparatuses of the present invention. As provided above, the preferred range of vibration amplitude is of about 0.1 mm to about 10 mm. A skilled artisan can readily adapt any amplitude modulation means for use with a particular vibration means in the present apparatuses.

In addition, the apparatuses of the present invention will preferably contain frequency modulation means. Frequency modulation means are used to control the frequency of the vibration applied to the skin surface. As provided above, the preferred vibration frequency is from about 1 Hz to about 100 Hz. A skilled artisan can readily adapt any frequency modulation means for use with a particular vibration means in the present apparatuses.

Figure 7:
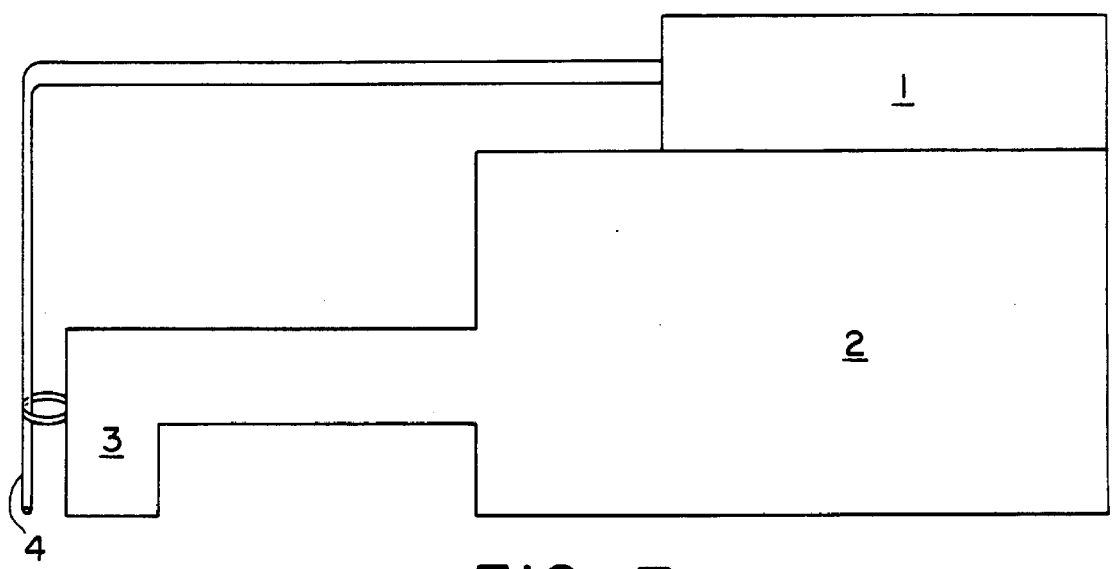
FIG. 7 shows a diagrammatic representation of a configuration of the apparatuses of the present invention.

The apparatuses of the present invention will be configured such that the vibration means are connected in some fashion to the application means. The configuration and means of attachment will primarily be based on the application means and vibration means chosen. The exact configuration is only limited by the need to include the elements that make up the application means and the vibration means in the apparatus. FIG. 7 provides a diagrammatic representation of a one possible configuration of an apparatus of the present invention. An application means (1) is connected to a vibration means (2). The application means applies an agent to the skin surface through applicator (4). The vibration means provides vibration to the skin surface using a vibration applicator (3).

The apparatuses of the present invention are preferably hand-held, being powered by an internal battery source or an external electrical source using an electrical cord. A hand-held configuration allows a greater ease of using the device of the present invention.

The apparatuses of the present invention further contains application means. As used herein, application means refers to any means for applying a particular agent to the skin surface being treated. Application means known in the art include, but are not limited to, dispensers which dispense the agent as either a liquid or mist. The apparatuses means will be selected based on the nature of the agent that is being administered. Particularly well suited are aerosol-type dispenser means powered by either pressurized gas or by a mechanical pump. A skilled artisan can readily adapt any application means known in the art in order to produce the apparatuses of the present invention.

The apparatuses of the present invention may further include an irradiation means that is either 1) part of the combined vibration and application means, 2) packaged in a kit containing the combined application means and vibration means or 3) that is packaged with separated vibration means and application means. As provided above, a photosensitizing agent can be selectively and efficiently delivered to a hair follicle using the vibration methods/apparatuses of the present invention. The sensitizing agent is irradiated using the irradiation means so as activate the agents, for example to ablate the hair follicle and removal unwanted hair. Accordingly, an irradiation means can either 1) be provided as a component of the apparatuses of the present invention such that the application means, vibration means and irradiation means are housed in a single unit, 2) be combined with any of the individual component used in the present method, for example vibration means and irradiation means in a single unit, or 3) be packaged in a kit with each of the other components provided separately.

The choice of the irradiation means will be based primarily on the choice of photosensitizing agents used. The irradiation means will be chosen so as to be capable of delivering the necessary electromagnetic irradiation to the treatment area. A skilled artisan can readily incorporated an irradiation means such as a low voltage laser into the apparatuses of the present invention.

The present invention further provides kits that contain each of the components used in the methods of the present invention. Specifically, the present invention provides a kit packaged to contain a vibration means and an application means, provided as separate components or as a single unit. The kit may further contain irradiation means and one or more agents that is to be delivered to the hair follicles. A skilled artisan can readily assemble a kit that contains the components used in the present methods.

The following examples are intended to illustrate, but not limited, the scope of the inventions disclosed and claimed herein.

EXAMPLES

Example 1

Figure 2A:
FIG. 2 shows the delivery of melanin into mouse hair follicles by skin vibration. A—control; B—melanin accumulation after hair removal by waxing; C—melanin accumulation after clipping hair
Figure 2B:
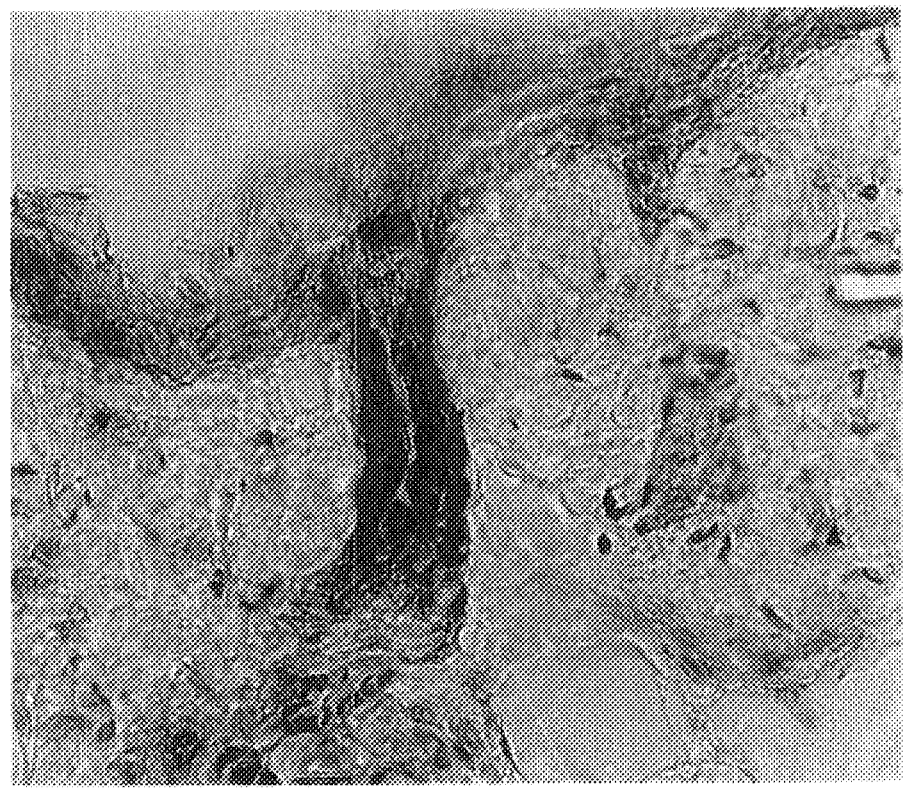
Figure 2C:
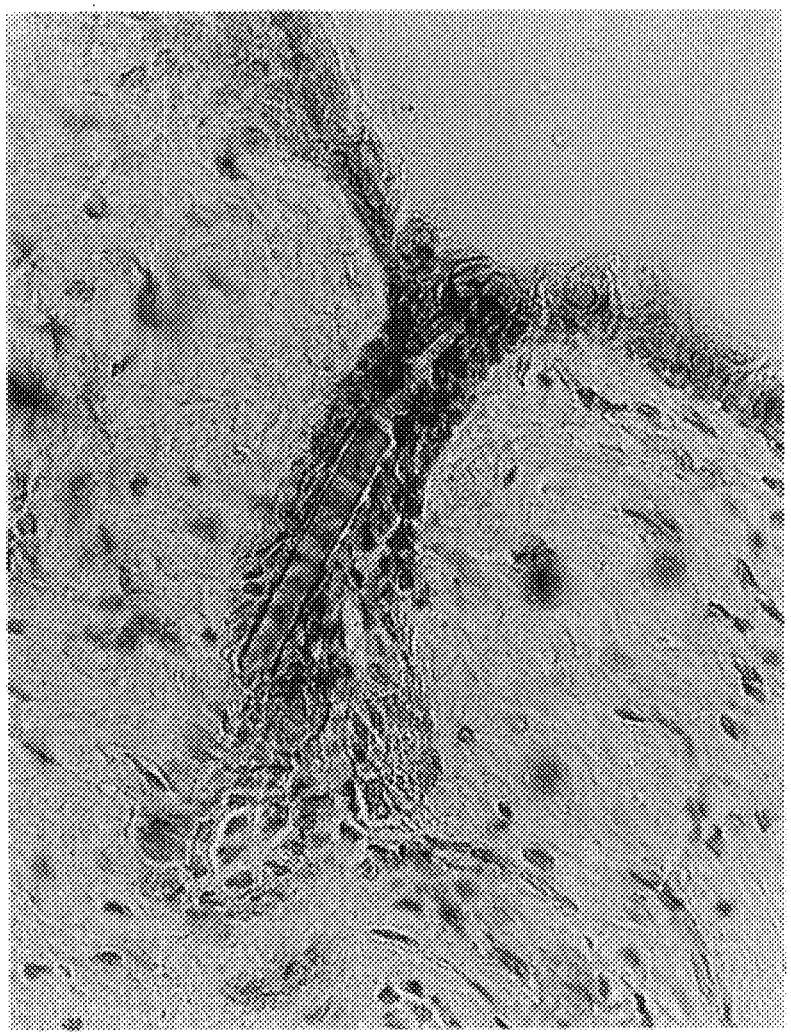

Protocol
1. Preheat wax mixture up to the temperature 50°–60° C.
2. Anesthetize mouse (Balb/C white mice strain was used) with isoflurane.
3. Apply hot wax onto the top of working hair area on the mouse back.
4. Peel off the waxed hair in the direction from the tail to the head.
5. Clean the working skin area with 70% isopropyl alcohol with a pad.
6. Apply cyanoacrylate based glue onto the circular edge of a plastic chamber, see FIG. 1.
7. Firmly attach the edge of the plastic chamber with the glue to the mouse skin.
8. Wait 2–3 min until glue dries (make sure that there is no space/air bubbles left between the edge of the chamber and mouse skin).
9. Pour ~0.3–0.5 ml of a solution containing a test agent into the chamber. Melanain, India ink and carbon particles where used.
10. Apply vibration, BodyMate™ Power messager, model PM-606 vibration brush (HomeMedics Inc., 2240 Greer Blvd. Keego Harbor, Mich. 48320) with mounted head with attached plastic bristles of diameter 0.2 mm (see FIG. 1) in high power mode with vibration frequency 10 Hz and amplitude 1 mm to the mouse skin covered by carbon solution in circular and forward-backward directions for 5 minutes.
11. Remove the chamber and clean the examined skin surface area from the carbon.
12. Excise the skin samples for histological staining.
13. Make frozen sections.
14. Counter-stain slides with 0.1% nuclear fast red.
15. Microscopy and photography Results FIG. 2 shows the targeted delivery of melanin into mouse hair follicles by skin vibration. As shown in FIG. 2, melanin was delivered approximately half-way down to the hair follicles in both the waxing (FIG. 2B) and clipped mice (FIG. 2C). In contrast, as shown in FIG. 2A, no melanin was delivered into the mouse hair follicles by passive diffusion even at 1 hour after the topical application of melanin.

Figure 3A:
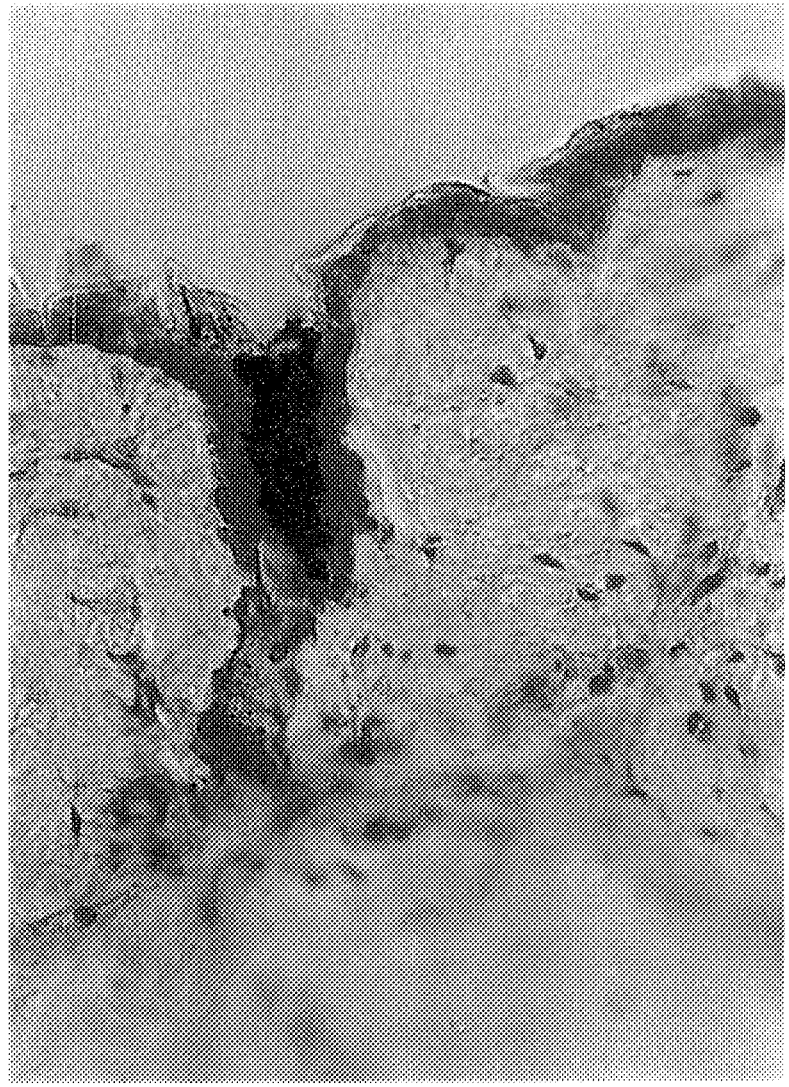
FIG. 3 shows the delivery of India ink particles into mouse hair follicles by skin vibration. A—follicular accumulation after hair removal; B—follicular accumulation after clipping hair
Figure 3B:
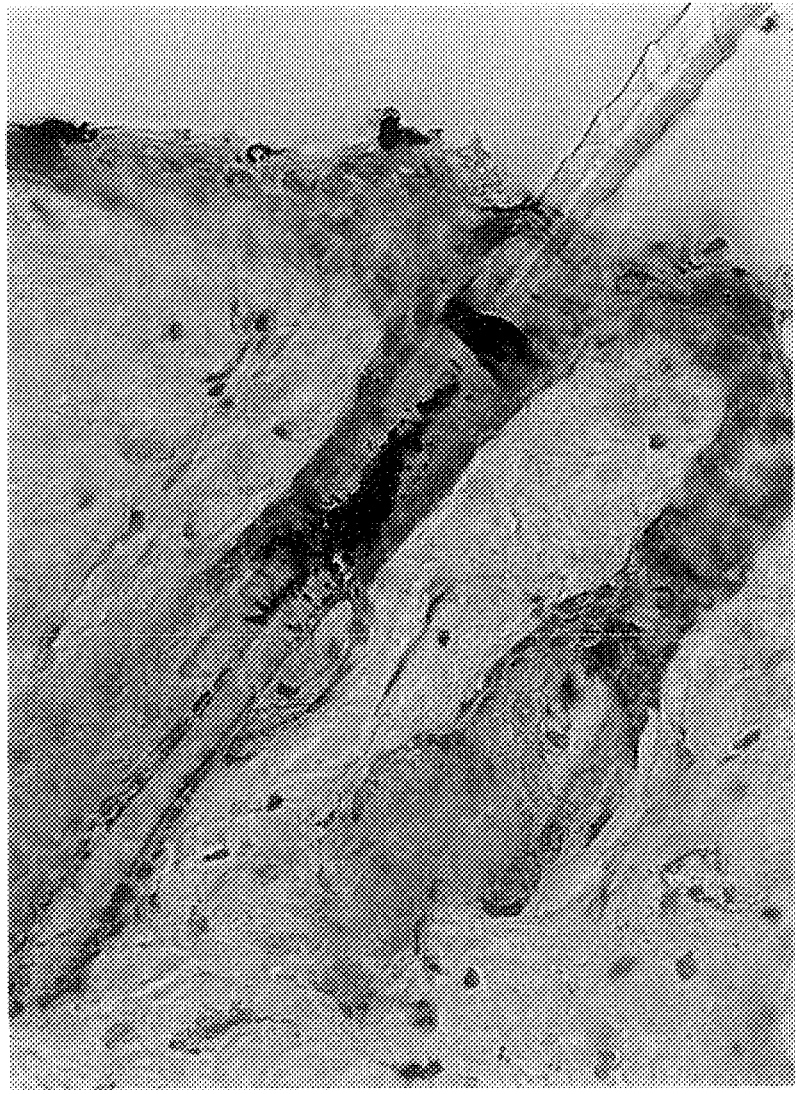
Figure 4A:
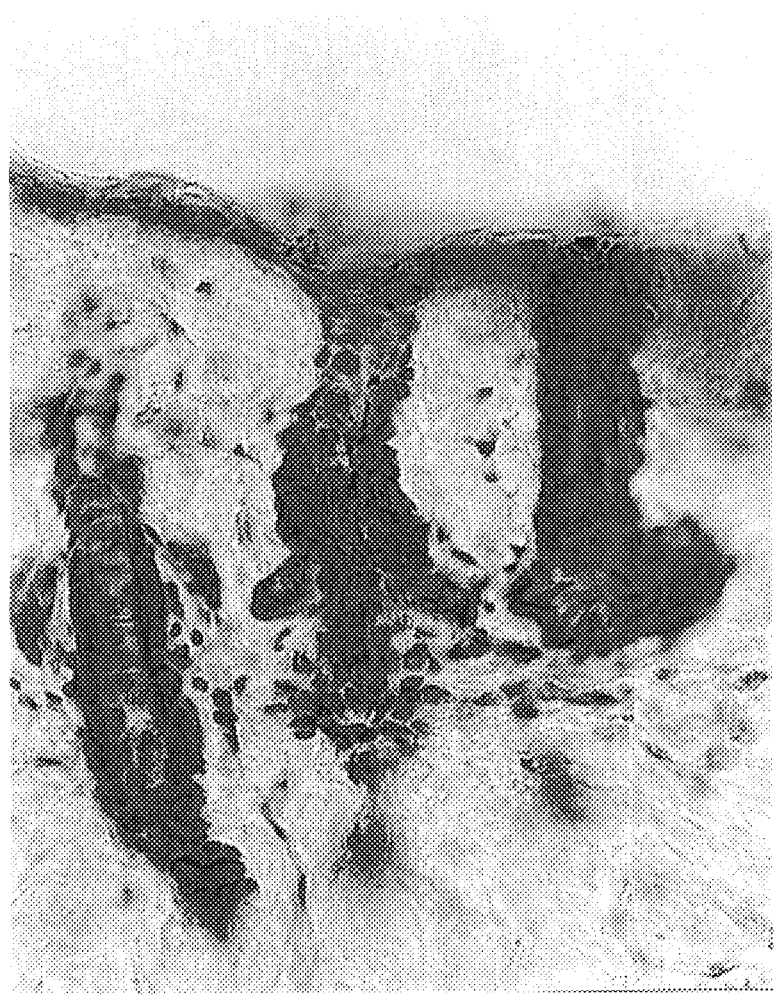
FIG. 4 shows the delivery of carbon particles into mouse hair follicles by vibration massage. A—follicular accumulation after hair removal; B—follicular accumulation after clipping hair

The results shown in FIG. 3 (with black India ink particles) and FIG. 4 (with carbon particles) are typical results obtained for the delivery of carbon particles or ink particles into waxed mouse hair follicles using skin vibration. FIG. 3A (India ink particles) and FIG. 4A (carbon particles) show the delivery of particles in waxed mice. These agents are used to demonstrate the selectivity and degree of delivery of an agent into hair follicles lacking hair growth using co-administered vibration.

Figure 4B:
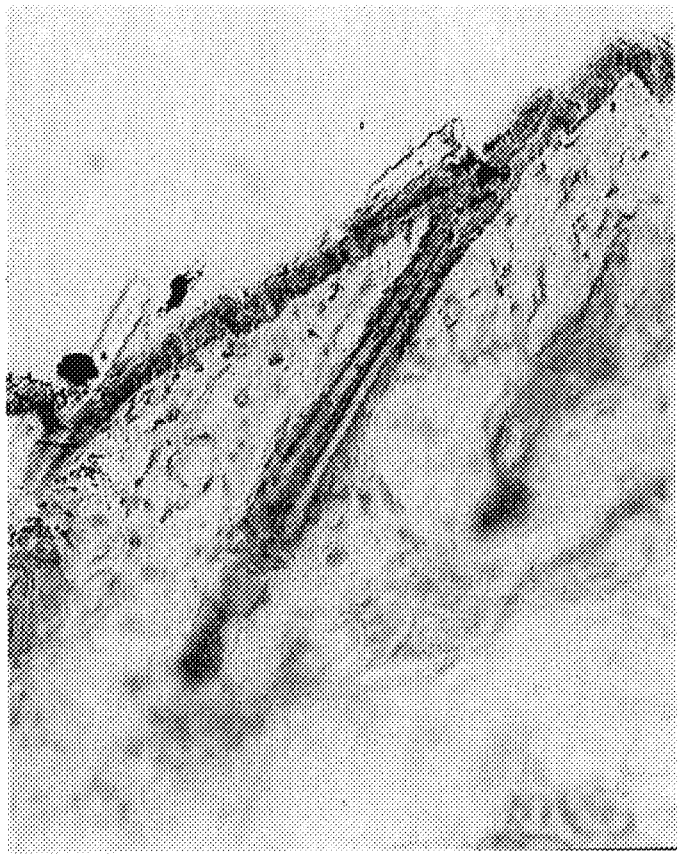

FIG. 3B (black India ink particles) and FIG. 4B (carbon particles) are typical results obtained for the delivery of carbon particles or ink particles into clipped mouse hair follicles using skin vibration. As evidence in the Figures, in case of India ink (as shown in FIG. 3), almost all hair follicles contain ink particles to a great extent. Carbon particles are observed in the hair follicle as well but to a less extent compared to India ink particles. These particles are used to demonstrate the selectivity and degree of delivery of an agent into hair follicles having hair growth using co-administered vibration.

The greater level of India ink accumulation in the hair follicles compared to carbon particles can be explained by the fact that the average size of India Ink particles (~0.2 um) is about an order less than carbon particles (2 um). In both cases ink and carbon particles were not observed in the epidermis and dermis, but only in the hair follicles.

Figure 5:
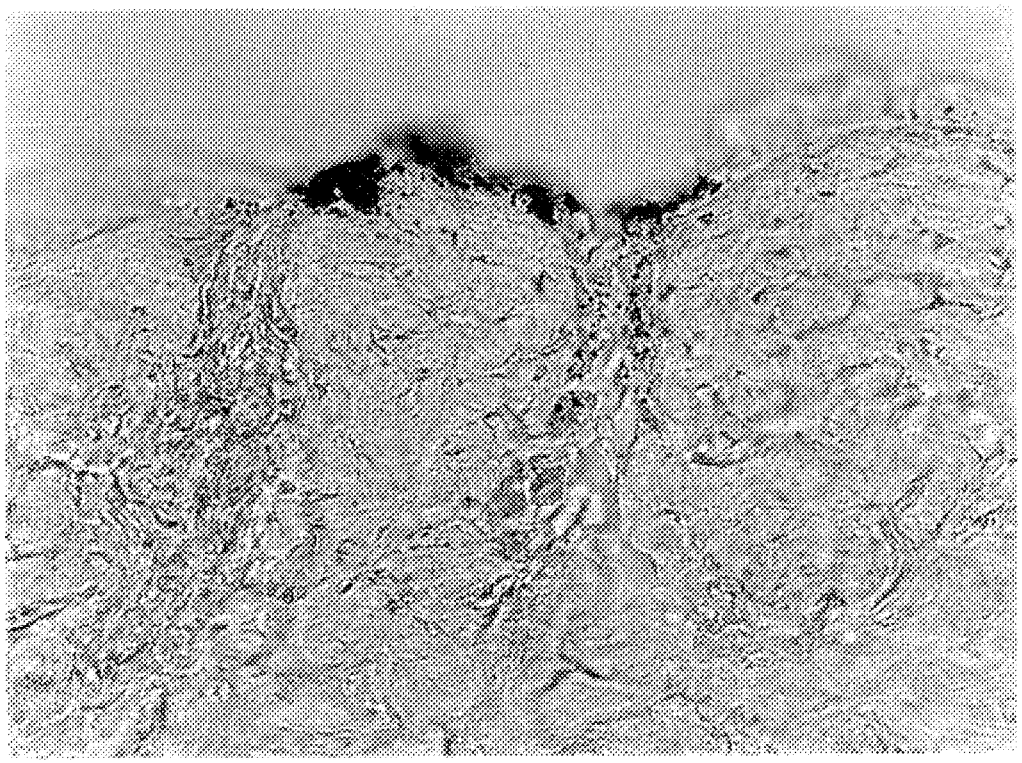
FIG. 5 shows the delivery of carbon particles in liposomes into mouse hair follicles by skin vibration.

FIG. 5 demonstrate that the carbon particles with liposomes were delivered into hair follicles after skin vibration. In comparison to carbon particles without liposomes as shown in FIG. 4, carbon particles with liposomes seem to have a higher level of accumulation (FIG. 5).

Our results showed that skin vibration is effective after both removing hair by wax or clipping hair. The delivery of substances into the hair follicles of mice is effective even after skin vibration for 5 minutes. Thus the method provides a fastest an effective means for delivering agents selectively into hair follicles.

Example 2

The use of vibrational delivery of agents to hair follicles was used in combination with electromagnetic irradiation as a means of ablating hair follicles. A mouse was waxed as described above and four treatment areas were defined. In one area, no agent was applied but the area was irradiated with a laser. A continuous pulsing laser, model LT 100-A (LORAD, Danbury, Conn.), was used to deliver approximately 30 pulses at 0.1 J/pulse, pulse time of <1 minute in duration, at a wavelength of 1060 nm, to the treatment area (area 1, FIG. 6). In a second area, India ink was applied using vibration for 5 minutes as described above and the area was irradiated with a laser as described for area 1 (area 2, FIG. 6). In a third area, carbon particle were administered with 5 minutes of vibration as described above and the area was irradiated with a laser as described for area 1 (area 3, FIG. 6). In the fourth no agent or laser was used.

The result provided in FIG. 6 show that the hair density is dramatically reduced in density, length and thickness in the area treated with agent/vibration and irradiation. The results demonstrate that electromagnetic irradiation after delivery of a sensitizing agent to a hair follicle can be used as a means of hair follicle ablation and subsequent hair removal.

We claim:

1. A method to improve delivery of an agent to hair follicles, said method comprising the steps of administering said agent to an area of skin containing hair follicles, and applying vibration of from about 1 Hz to about 100 Hz with an amplitude of about 0.1 mm to about 10 mm in combination with said agent.

2. The method of claim 1 wherein said vibration is from about 5 Hz to about 20 Hz with an amplitude of about 0.5 mm to about 2 mm.

3. The method of claim 2 wherein said agent is selected from the group consisting of hair growth stimulator, hair growth inhibitors, genes for regulating hair growth, anti-alopecia agents, agents to restore natural hair pigment, agents to modify the color of hair and agents that remove unwanted hair.

4. The method of claim 3 wherein said agent is selected from the group consisting of minoxidil, substance-P, fenesteride, cyclosporin, melanin, tyrosinase, p21 protein, cell cycle inhibitors, cell proliferation inhibitors, anti-androgen agents and inhibitors of 5-α reductase.

5. The method of claim 1 wherein said vibration is about 10 Hz with an amplitude of about 1 mm.

6. The method of claim 5 wherein said agent is selected from the group consisting of hair growth stimulator, hair growth inhibitors, genes for regulating hair growth, anti-alopecia agents, agents to restore natural hair pigment, agents to modify the color of hair and agents that remove unwanted hair.

7. The method of claim 1 wherein said applied agent is a photosensitizing, photoreactive, or photoactivated agent, said method further comprising the step of administering electromagnetic irradiation to the skin following the application of vibration.

8. The method of claim 7 wherein said agent is selected from the group consisting of hair growth stimulator, hair growth inhibitors, genes for regulating hair growth, anti-alopecia agents, agents to restore natural hair pigment, agents to modify the color of hair and agents that remove unwanted hair.

9. The method of claim 7 wherein said agent is selected from the group consisting of minoxidil, substance-P, fenesteride, cyclosporin, melanin, tyrosinase, p21 protein, cell cycle inhibitors, cell proliferation inhibitors, anti-androgen agents and inhibitors of 5-α reductase.

10. The method of claim 1 wherein said agent is selected from the group consisting of hair growth stimulator, hair growth inhibitors, genes for regulating hair growth, anti-alopecia agents, agents to restore natural hair pigment, agents to modify the color of hair and agents that remove unwanted hair.

11. The method of claim 10 wherein said agent is selected from the group consisting of minoxidil, substance-P, fenesteride, cyclosporin, melanin, tyrosinase, p21 protein, cell cycle inhibitors, cell proliferation inhibitors, anti-androgen agents and inhibitors of 5-α reductase.

12. The method of claim 1 wherein said agent is selected from the group consisting of hair growth stimulator, hair growth inhibitors, genes for regulating hair growth, anti-alopecia agents, agents to restore natural hair pigment, agents to modify the color of hair, agents that remove unwanted hair, tyrosinase, p21 protein, cell cycle inhibitors, cell proliferation inhibitors, anti-androgen agents and inhibitors of 5-α reductase.

13. A method to improve delivery of an agent to hair follicles, said method comprising the steps of administering said agent to an area of skin containing hair follicles, and applying vibration at about 10 Hz with an amplitude of about 1 mm.

14. The method of claim 13 wherein said agent is selected from the group consisting of hair growth stimulator, hair growth inhibitors, genes for regulating hair growth, anti-alopecia agents, agents to restore natural hair pigment, agents to modify the color of hair, and agents that remove unwanted hair.

\* \* \* \* \*